United States Patent
DeLong Samalik et al.

(10) Patent No.: US 11,903,882 B2
(45) Date of Patent: Feb. 20, 2024

(54) METHODS AND SYSTEMS FOR AN ADJUSTABLE HEAD HOLDER

(71) Applicant: GE Precision Healthcare LLC, Milwaukee, WI (US)

(72) Inventors: Michelle DeLong Samalik, Milwaukee, WI (US); Ronald Kulas, Delafield, WI (US); Sharon Ghelman, Hollywood, FL (US); Kelly Vonderhaar Kaiser, Wauwatosa, WI (US); Vishwanath Nayak, Bangalore (IN); Dhaval Pravinbhai Dangashiya, Gujarat (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 529 days.

(21) Appl. No.: 16/847,508

(22) Filed: Apr. 13, 2020

(65) Prior Publication Data
US 2021/0315530 A1    Oct. 14, 2021

(51) Int. Cl.
  *A61G 13/12*   (2006.01)
  *A61B 6/04*    (2006.01)
  *A61B 5/00*    (2006.01)

(52) U.S. Cl.
  CPC .......... *A61G 13/121* (2013.01); *A61B 5/702* (2013.01); *A61B 6/0407* (2013.01)

(58) Field of Classification Search
  CPC .... A61G 13/121; A61B 6/0407; A61B 6/0428
  See application file for complete search history.

(56) References Cited

U.S. PATENT DOCUMENTS

| | | | | |
|---|---|---|---|---|
| 5,785,041 | A * | 7/1998 | Weinstein | A61B 8/0875 600/407 |
| 9,913,620 | B2 | 3/2018 | Smith et al. | |
| 2006/0083355 | A1* | 4/2006 | Loser | A61B 6/0442 378/208 |
| 2008/0172791 | A1* | 7/2008 | Walczyk | A61G 13/12 5/624 |
| 2016/0374630 | A1* | 12/2016 | Smith | A61B 6/0407 378/208 |

(Continued)

FOREIGN PATENT DOCUMENTS

| | | | | |
|---|---|---|---|---|
| JP | | 61288838 A | 12/1986 | |
| WO | WO-9911176 A1 * | | 3/1999 | A61B 6/0421 |

OTHER PUBLICATIONS

EP application 21165706.9 filed Mar. 29, 2021—Extended Search Report dated Aug. 8, 2021; 8 pages.

(Continued)

*Primary Examiner* — Justin C Mikowski
*Assistant Examiner* — Adam C Ortiz

(57) ABSTRACT

Various systems are provided for an adjustable tilting head holder. In one example, a system comprises an adjustable tilting head holder for use with an imaging system the adjustable head holder comprising a head cradle, a tilt adjustment mechanism with a plurality of locking positions arranged below a first end of the head cradle, a table mount extending from a second end of the head cradle, and a tilt adjustment bar that extends from the table mount through the tilt adjustment mechanism, wherein the first end and the second end of the head cradle are located at opposite ends of the head cradle.

14 Claims, 9 Drawing Sheets

(56) References Cited

U.S. PATENT DOCUMENTS

2019/0313985 A1* 10/2019 Bardo .................. A61B 6/032
2021/0077333 A1* 3/2021 Kumar ................ A61G 15/125

OTHER PUBLICATIONS

Wagner, G. et al., "An Ornamental Design for a Head Holder Pad," U.S. Appl. No. 29/670,467, filed Nov. 15, 2018, 25 pages.
JP application 2021-065013 filed Apr. 6, 2021—Office Action dated Jan. 6, 2023, Machine Translation Jan. 7, 2023; 4 pages.
JPS61288838A—Machine Translation, Mar. 17, 2023; 3 pages.

\* cited by examiner

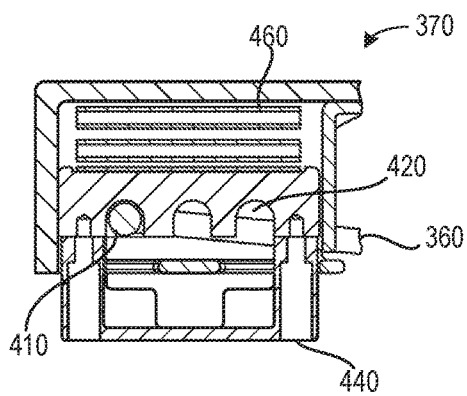
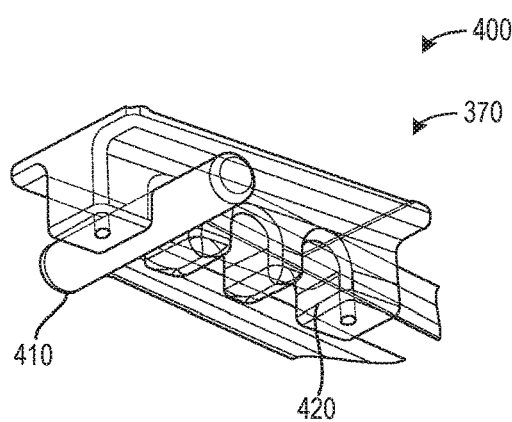
FIG. 4A  FIG. 4B
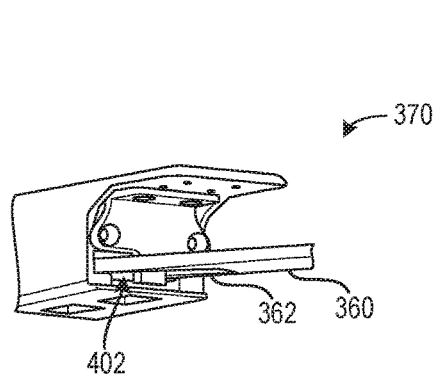
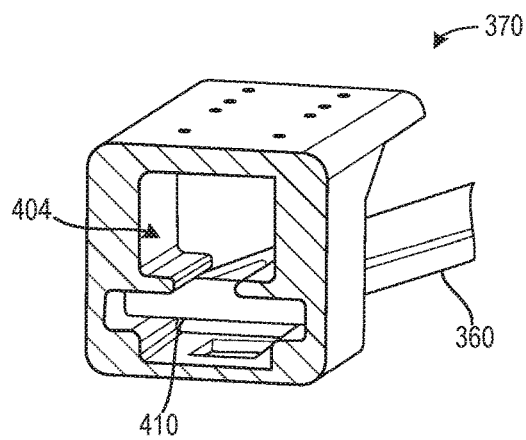
FIG. 4C  FIG. 4D
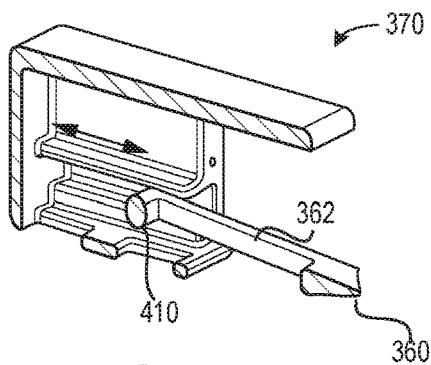
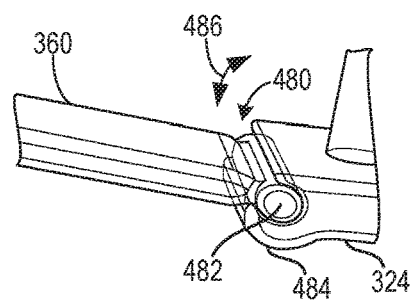
FIG. 4E  FIG. 4F
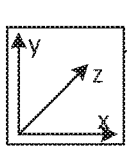

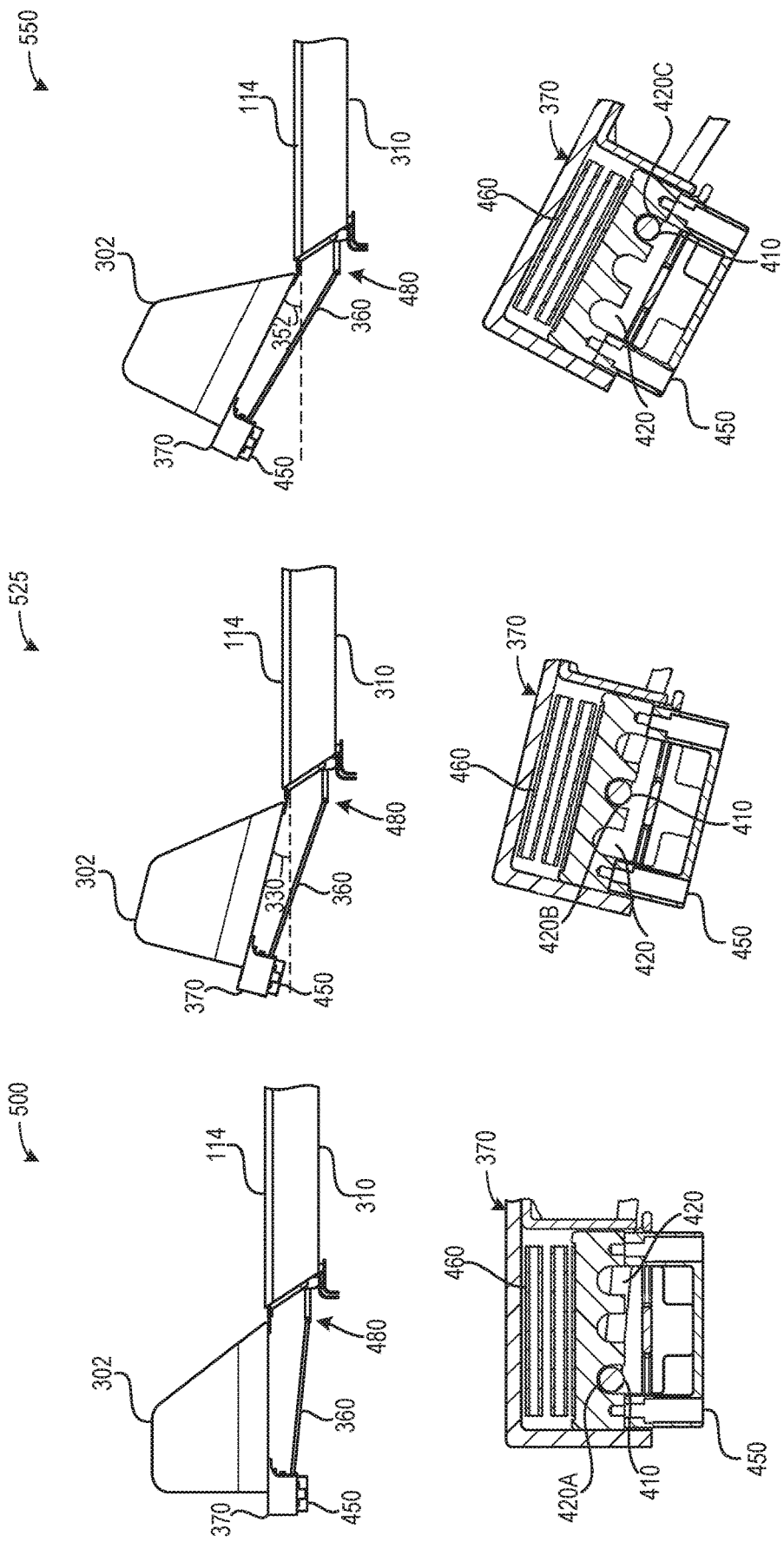

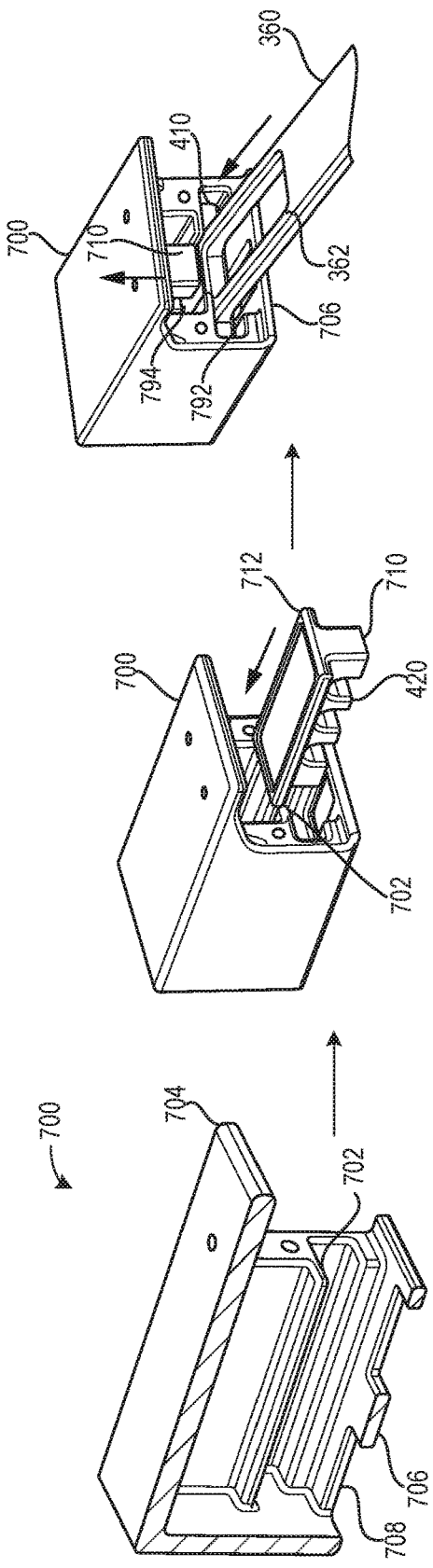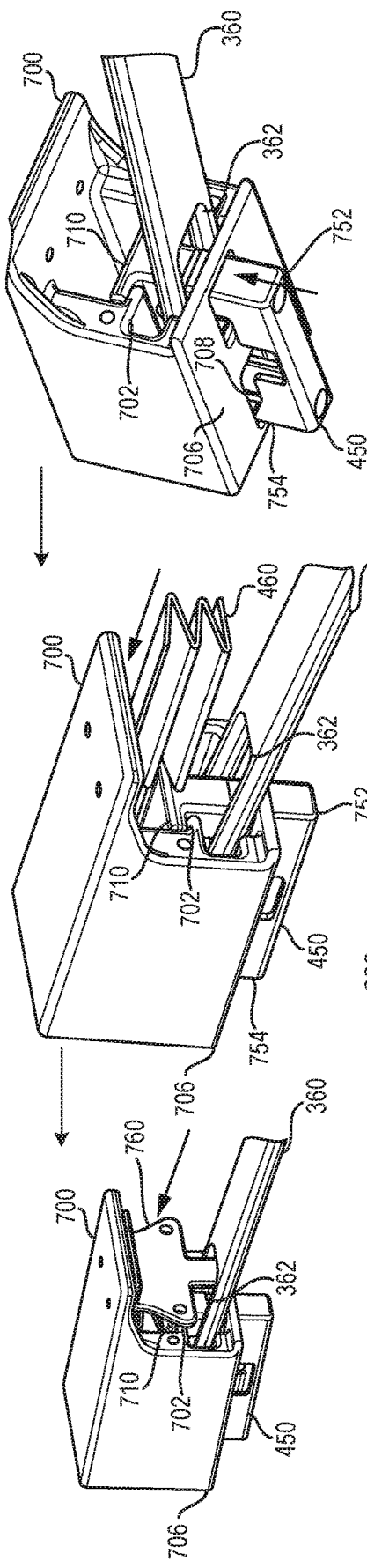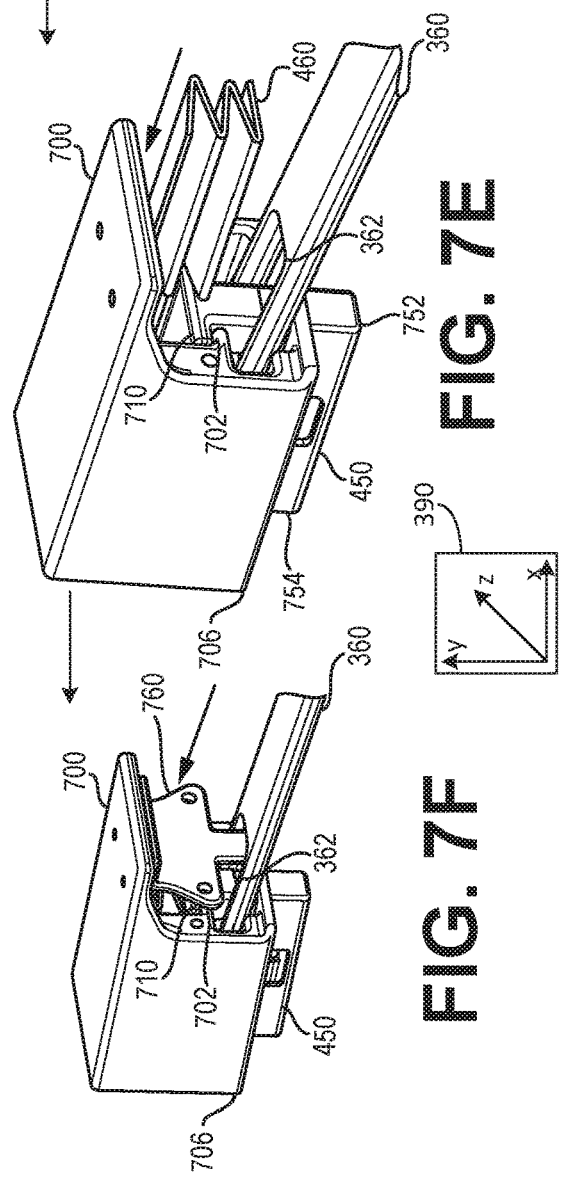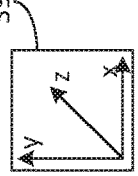

METHODS AND SYSTEMS FOR AN ADJUSTABLE HEAD HOLDER

CROSS-REFERENCE TO RELATED APPLICATIONS

The present application incorporates by reference in its entirety for all purposes U.S. Design application Ser. No. 29/731,209, entitled HEAD HOLDER, filed concurrently herewith.

TECHNICAL FIELD

Embodiments of the subject matter disclosed herein relate to an adjustable tilting head holder with a locking mechanism.

BACKGROUND

Adjustable head holders may be used in a variety of environments. Adjustable head holders may be used during imaging scans to support and position a patient's head through a range of discrete angles. The ability to tilt a patient's head and hold that position throughout an imaging scan is very important for image quality. In one example, adjustable head holders may be used in a medical setting to adjust the position of a patient's head to avoid imaging dental implants and other devices that may create image artifacts during a medical imaging procedure. In addition, tilting a patient's head may allow a reduction in radiation dose to a sensitive anatomy, such as the eyes by placing them outside of the x-ray radiation beam. An adjustable head holder allows an imaging technologist or operator to position a patient's head in such a way that without the device, the patient would not be able to hold his/her head in a specific orientation during a scan. Other patients who would benefit from the use of an adjustable head holder can be subject to involuntary movements or may be combative. Having a positive locking mechanism ensures that patients subject to the above conditions cannot change the tilting angle of the adjustable head holder themselves. A further benefit to the adjustable head holder is that some of the positions in which the patient's head is positioned via the head holder may be uncomfortable without support from the head holder.

BRIEF DESCRIPTION

In one embodiment, a system comprises an adjustable head holder for use with an imaging system the adjustable head holder comprising a head cradle, a tilt adjustment mechanism with a plurality of locking positions arranged below a first end of the head cradle, a table mount extending from a second end of the head cradle, and a tilt adjustment bar that extends from the table mount through the tilt adjustment mechanism, wherein the first end and the second end of the head cradle are located at opposite ends of the head cradle.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 4A, 4B, 4C, 4D, and 4E show different views of a locking mechanism of the first embodiment of the adjustable head holder;

FIG. 4F shows a ball joint of the first embodiment of the adjustable head holder;

FIGS. 5A, 5B, and 5C show various positions of the first embodiment of the adjustable head holder based on a position of the locking mechanism;

FIGS. 7A, 7B, 7C, 7D, 7E, and 7F show an assembly of the locking mechanism of the first embodiment of the adjustable head holder;

FIGS. 3A to 12 are shown to scale, however, other relative dimensions may be used if desired.

DETAILED DESCRIPTION

Figure 6A:
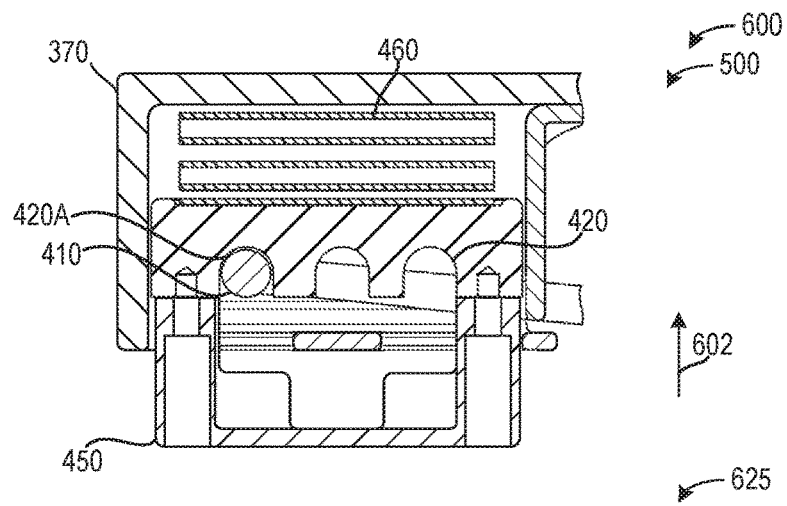
FIGS. 6A, 6B, and 6C show an adjustment of the locking mechanism from a first position to the second position of the first embodiment of the adjustable head holder.
Figure 6B:
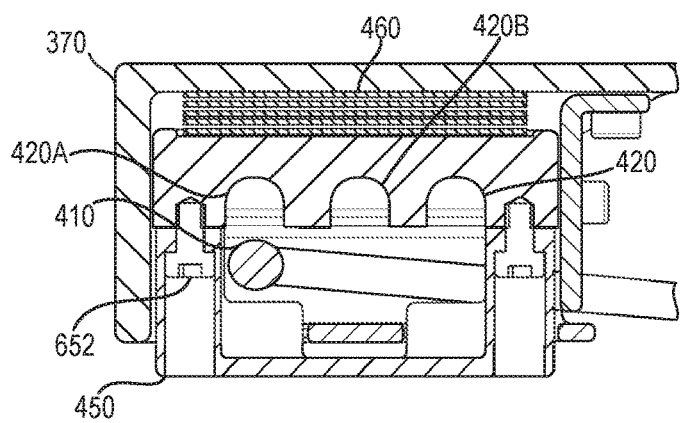
Figure 6C:
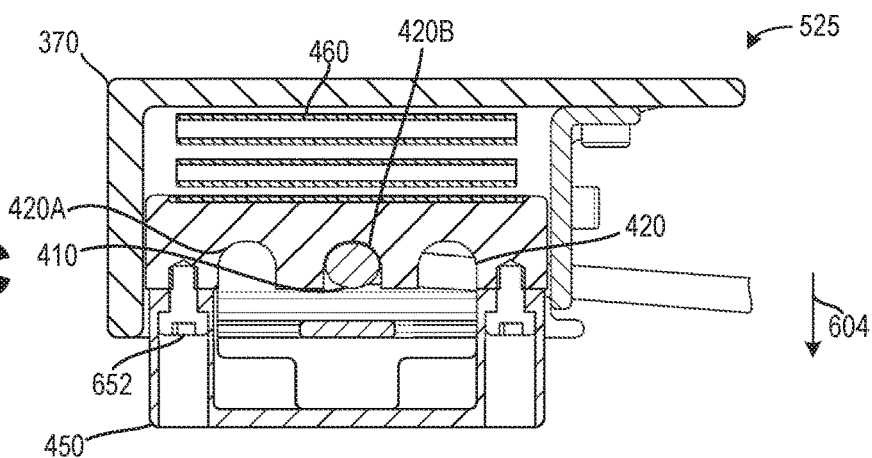
Figure 6D:
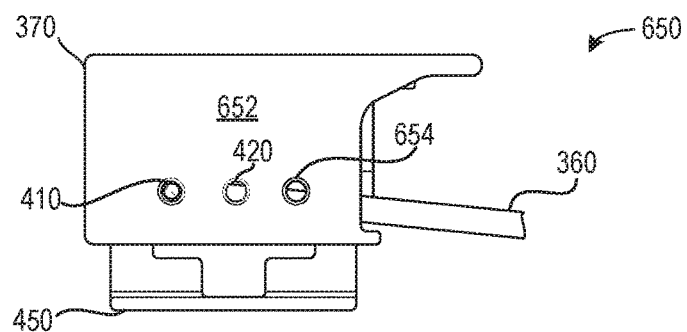
FIG. 6D shows a side view of the locking mechanism of the first embodiment of the adjustable head holder.
Figure 8:
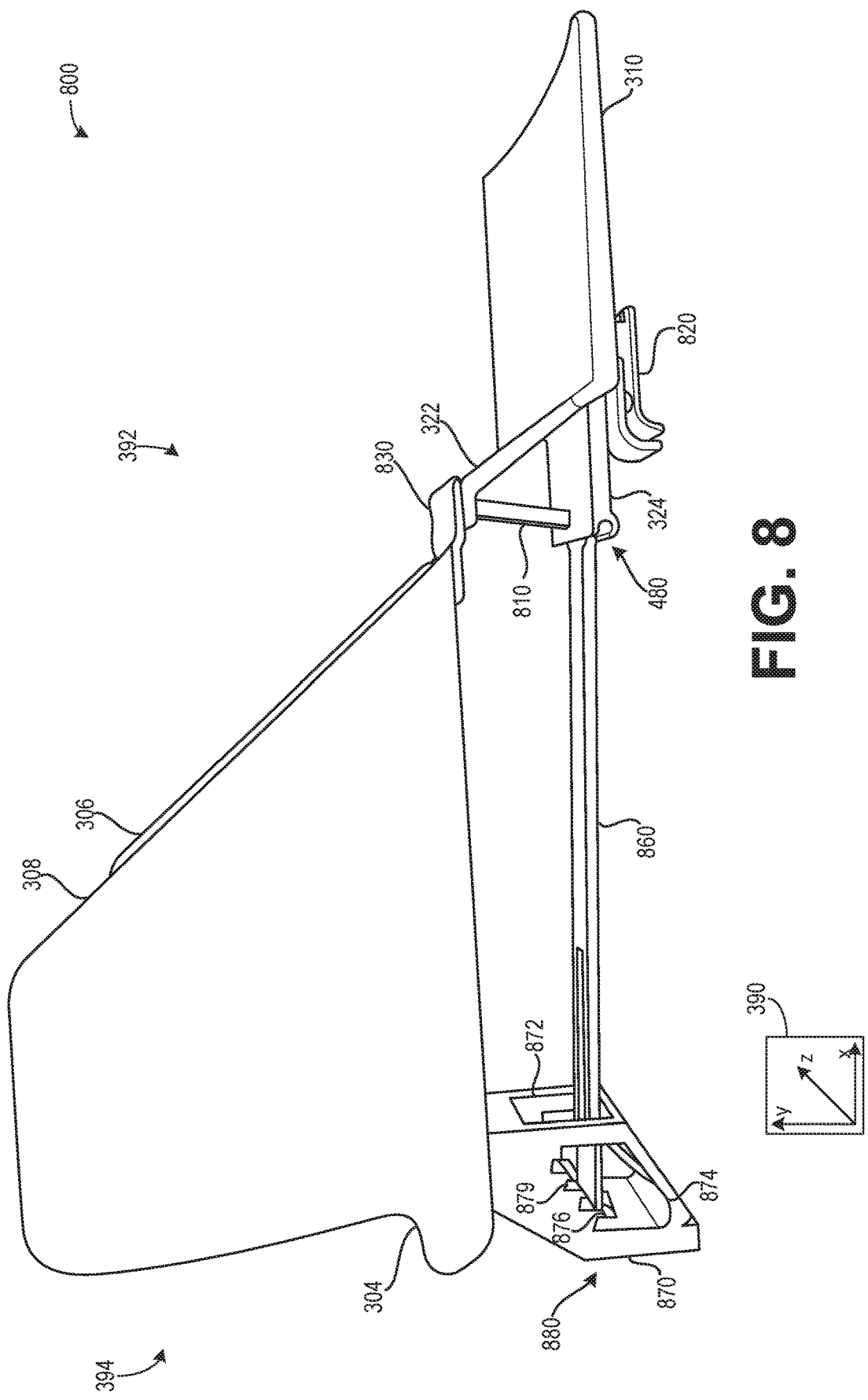
FIG. 8 shows a second embodiment of the adjustable head holder.
Figure 9:
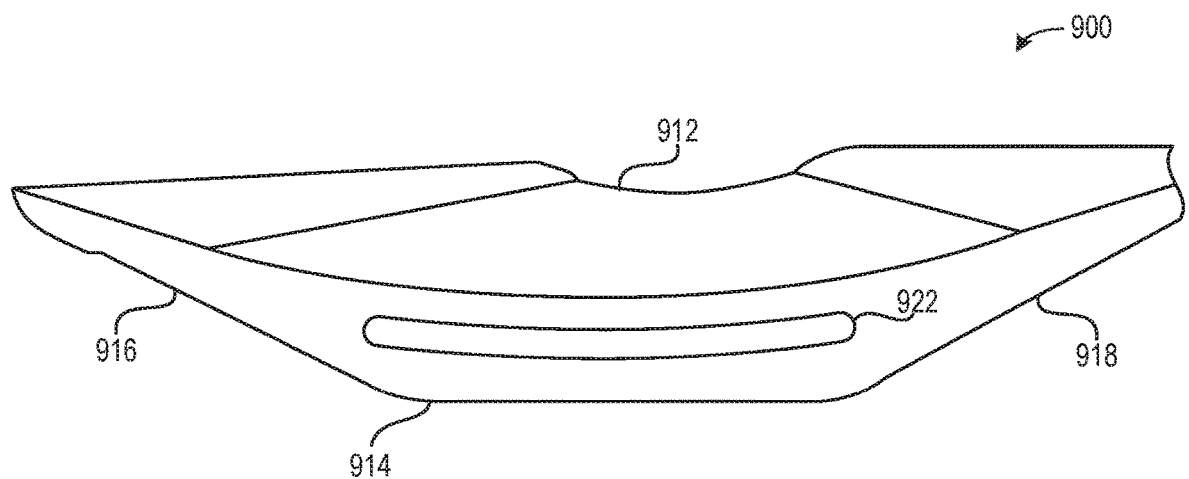
FIG. 9 shows a mount configured to couple to the first or the second embodiments of the adjustable head holder.
Figure 10:
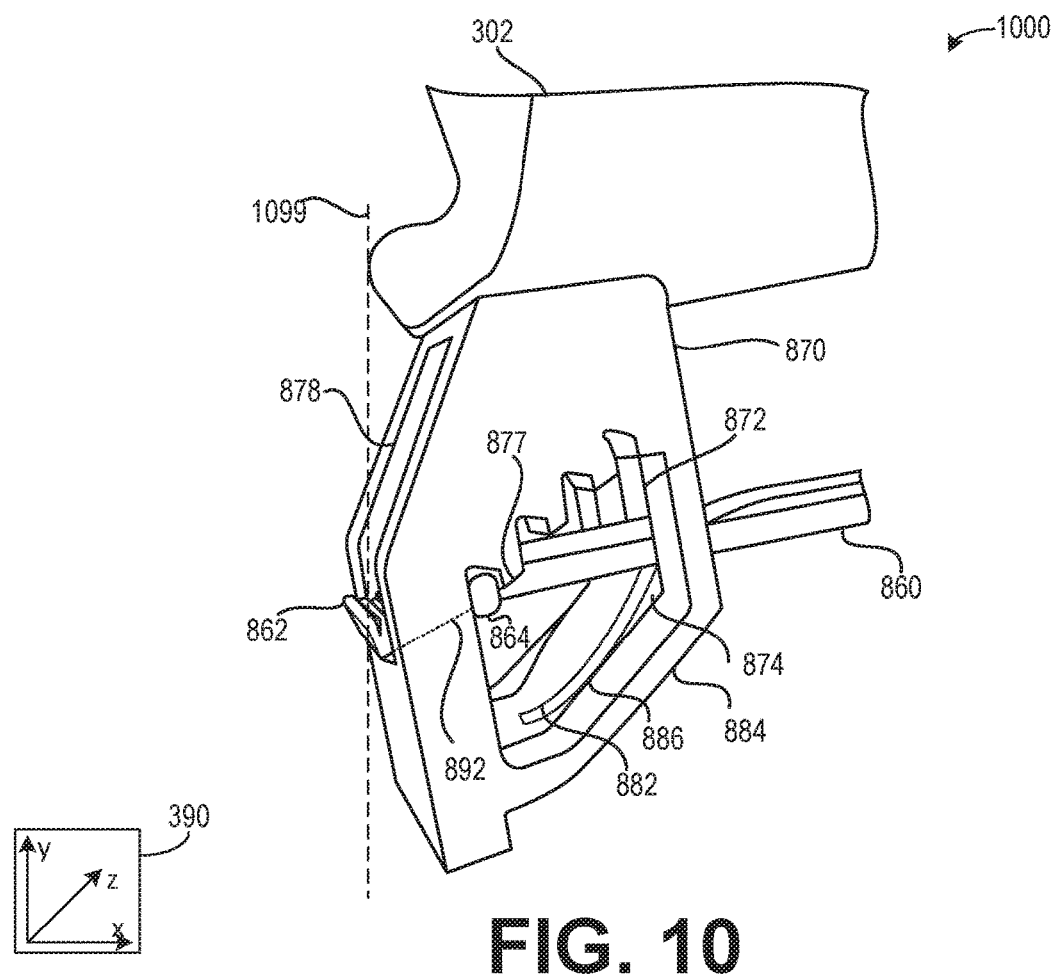
FIG. 10 shows a locking mechanism of the second embodiment of the adjustable head holder.
Figure 11:
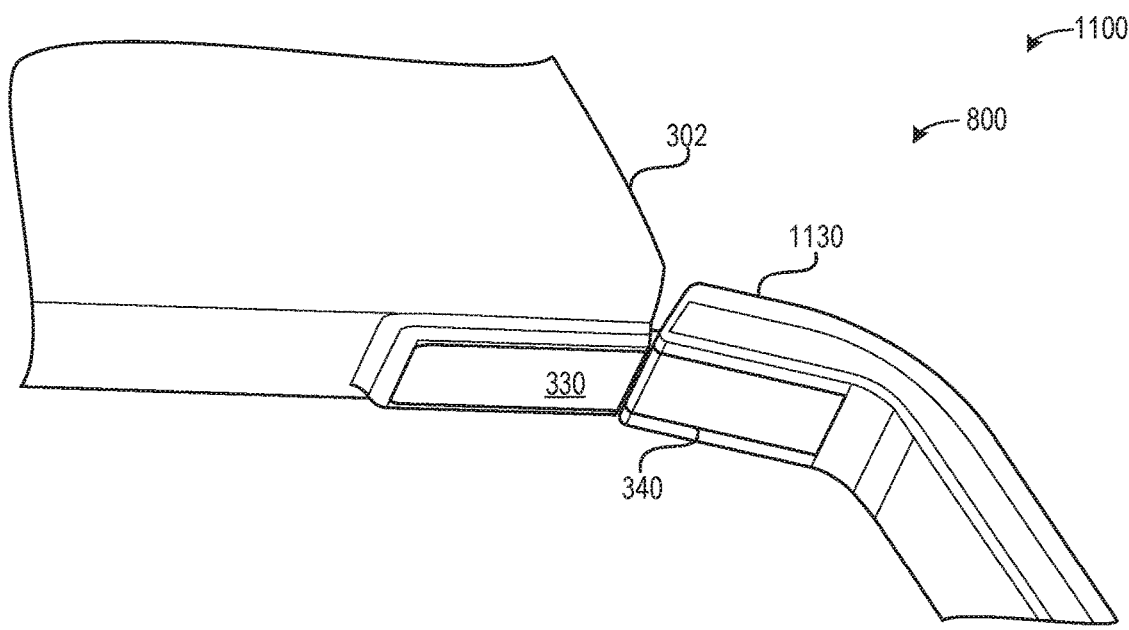
FIG. 11 shows a detailed view of a hinge of the first and second embodiments of the adjustable head holder.
Figure 12:
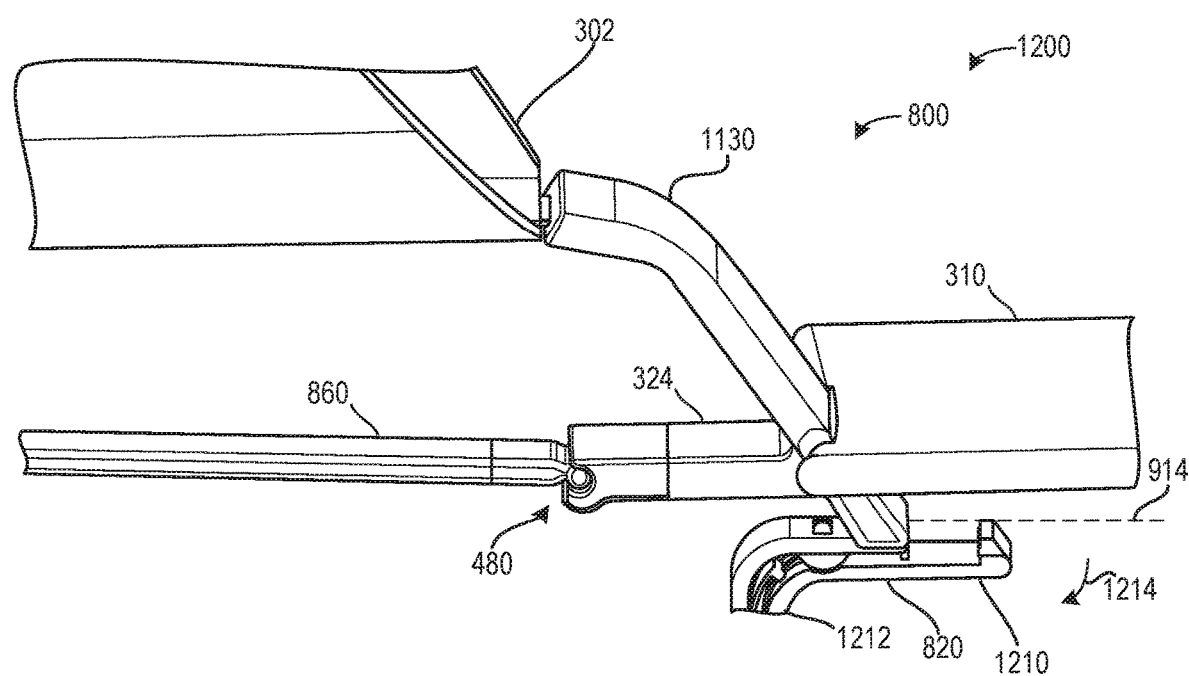
FIG. 12 shows a side-on view of the first and second embodiments of the adjustable head holder.

The following description relates to embodiments of an adjustable head holder. In one example, the adjustable head holder is an adjustable tilting head holder for an imaging system, such as a CT imaging system illustrated in FIGS. 1 and 2. A first example of the adjustable head holder comprises a cradle, a tongue insert, angle block, tilt bar, and a living hinge, as shown in FIGS. 3A and 3B. A first embodiment of a locking mechanism of the first embodiment of the adjustable head holder is illustrated in FIGS. 4A-4E. A ball joint about which the head may pivot is illustrated in FIG. 4F. FIGS. 5A through 5C illustrate various positions of the head based on an adjustment of the first embodiment of the locking mechanism. FIGS. 6A through 6C illustrate a transition of the first embodiment of the locking mechanism from a first position to a second position. FIG. 6D illustrates a position indicator arranged on an outside of the first embodiment of the locking mechanism. FIGS. 7A through 7F illustrate an assembly of the first embodiment of the locking mechanism. A second embodiment of the adjustable head holder is illustrated in FIG. 8. Therein, the second embodiment of the adjustable head holder may be substantially similar to the first embodiment of the adjustable head holder, except that the second embodiment comprises a locking mechanism different than the locking mechanism of the first embodiment of the adjustable head holder. A table mount configured to receive a table of either the first or second embodiment of the adjustable head holder is illustrated in FIG. 9. A detailed view of a second embodiment of the locking mechanism, which is different than the first embodiment of the locking mechanism, is illustrated in FIG. 10. FIG. 11 illustrates a detailed view of the living hinge, which may be included in each of the first and second embodiments of the adjustable head holder. FIG. 12 illustrates a side-on view of the table along with a tab which may be included in each of the first and second embodiments of the adjustable head holder.

In one example, the head holder may assist a radiologist to position a patient's head during computed tomography cranial x-ray examination. Previous examples include where a fixed head holder is used of an axial head scan in a CT imaging system having a tilting gantry mechanism to avoid directing x-ray radiation toward a patient's eyes. The tiltable head holder of the present disclosure ensures optimal positioning for neuro imaging in a CT imaging system and it adds more benefits in cases where the gantry is fixed and unable to tilt. The tiltable head holder may tilt the patient's head forward to align the brain anatomy with the scanners field of view. This minimizes radiation dose exposure to the eyes and may reduce image artifacts from dental implants. The head holder is free of metallic or sharp edge components within an imaging range. This is accomplished via a locking mechanism arranged directly below the head holder and out of an imaging range of a patient's head or neck. The angle adjustment of the locking mechanism may be between 0 to 45 degrees, however, other ranges may be utilized without departing from the scope of the present disclosure. A pivoting may occur via a revolute ball-type joint via actuation of a switch of the locking mechanism via a single hand of the operator.

The adjustable head holder to be used during imaging scans to support and adjust the patient's head through a range of discrete angles. The adjustable head holder has a positive locking mechanism, meaning that once a patient's head is properly positioned, the angle is locked in place and the patient is not able to change the angle by lifting his/her head out of the head holder.

FIGS. 1 and 3A through 12 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 1:
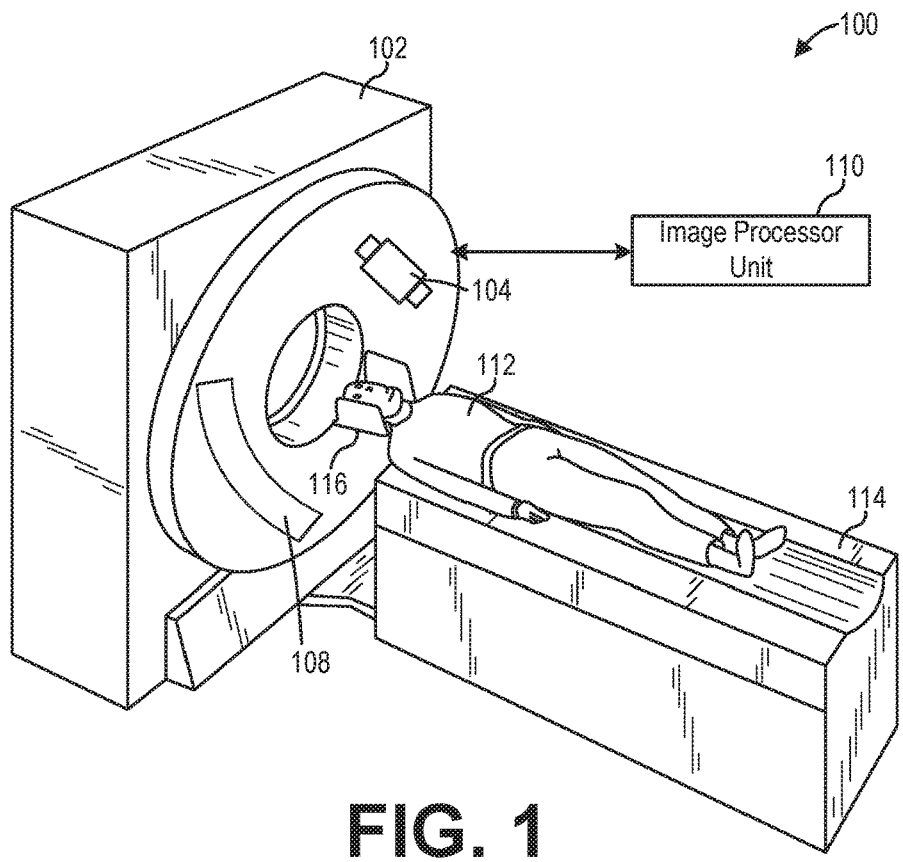
FIG. 1 shows a pictorial view of an imaging system, according to an embodiment.

FIG. 1 illustrates an exemplary CT imaging system 100 configured for CT imaging. Particularly, the CT imaging system 100 is configured to image a subject 112 such as a patient, an inanimate object, one or more manufactured parts, and/or foreign objects such as dental implants, stents, and/or contrast agents present within the body. In one embodiment, the CT imaging system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

In one example, table 114 may comprise a head holder 116 which may be adjustable (e.g., tiltable). Previous examples of tiltable head holders may be bulky, complex, or lacking auto-regulating features. Furthermore, the previous examples demand a greater amount of operator effort and the process may become cumbersome and time consuming. Additionally, the previous examples may need the operator to use both hands to adjust the head holder. If a patient moves their head when positioned in the head holder of a previous example, the adjustment mechanism may become free and a position of the head holder may change. This may result in the patient sliding off the table and into a CT gantry.

In one example of the present disclosure, as will be described below in greater detail with respect to FIG. 3A and the subsequent figures, a head holder may comprise a switch and automatic locking mechanism arranged directly below the head holder. The configuration may allow an operator to adjust the head holder angle with a single hand from either side of the patient table. The locking mechanism may not rely on gravity to maintain the head holder at the desired angle. The locking mechanism comprises a spring-based configuration which blocks the patient from adjusting the head holder when moving their head while strapped in.

Figure 2:
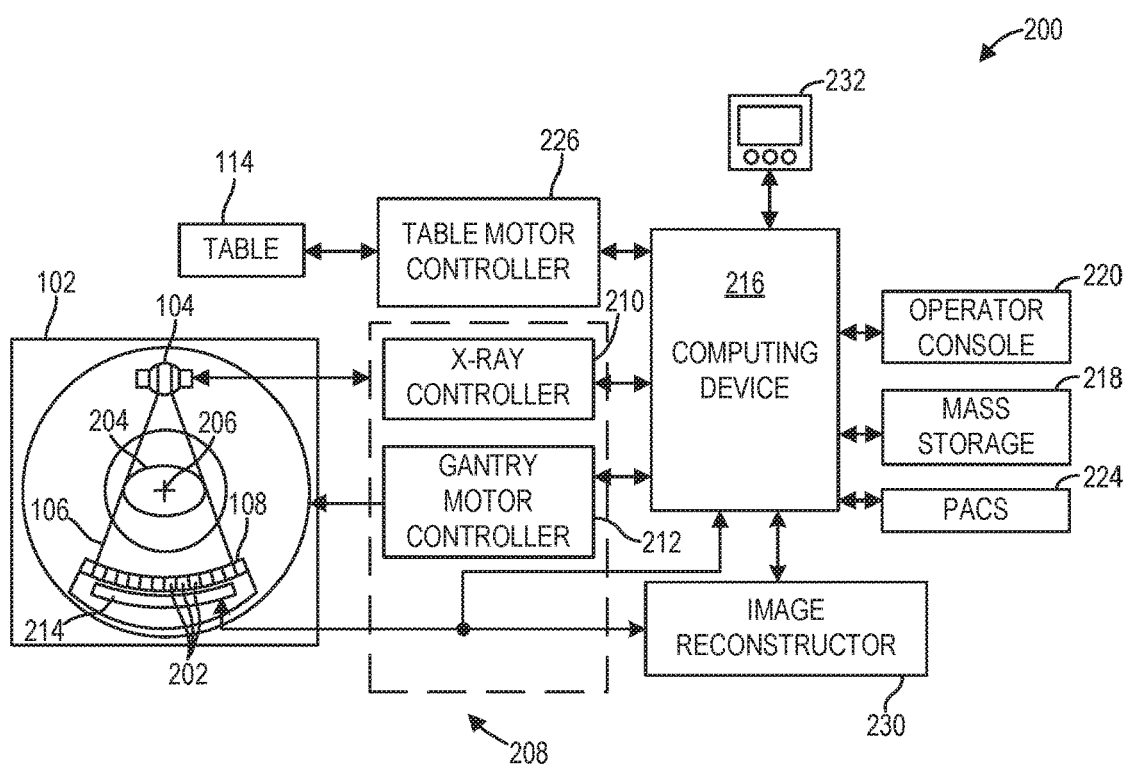
FIG. 2 shows a block schematic diagram of an exemplary imaging system, according to an embodiment.
Figure 3A:
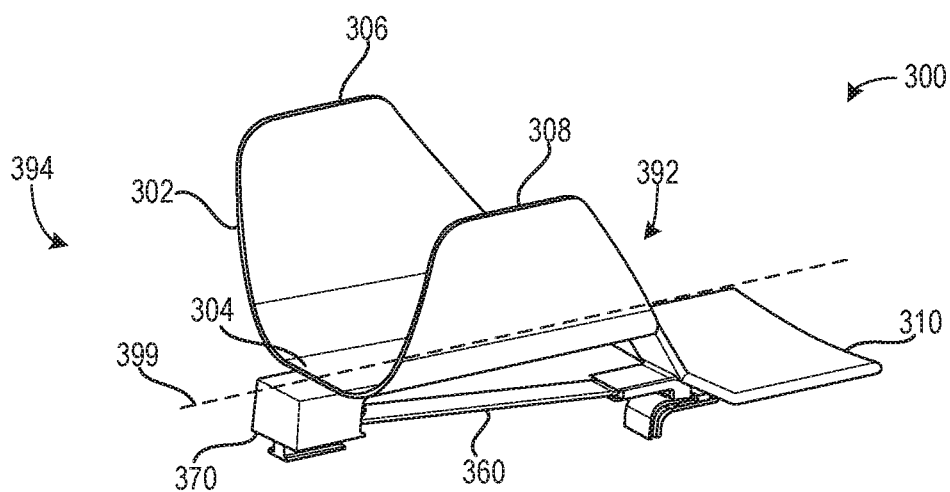
FIG. 3A shows a first view of a first embodiment of an adjustable head holder.
Figure 3B:
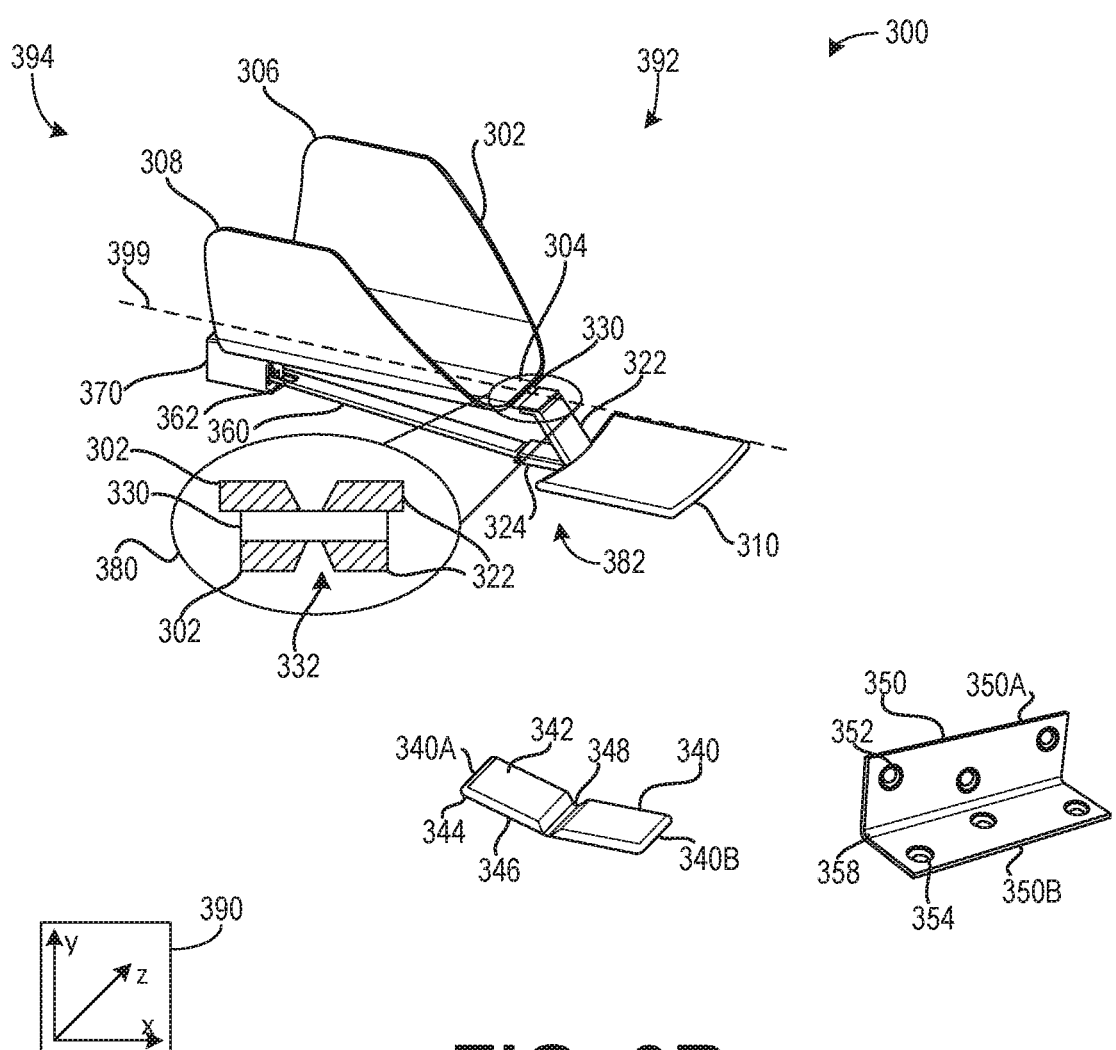
FIG. 3B shows a second view of the first embodiment of the adjustable head holder.

FIG. 2 illustrates an exemplary imaging system 200 similar to the CT imaging system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Though a CT system is described by way of example, it should be understood that the present technology may also be used on other imaging modalities, such as x-ray imaging systems, magnetic resonance imaging (MM) systems, nuclear medicine imaging systems, positron emission tomography (PET) imaging systems, single-photon emission computed tomography (SPECT) imaging systems, ultrasound imaging systems, and combinations thereof (e.g., multi-modality imaging systems, such as PET/CT or PET/MR imaging systems). The present discussion of a CT imaging modality is provided merely as an example of one suitable imaging modality.

The adjustable head holder is used on CT imaging systems that do not have a tilting gantry. Purpose is to support the head at a desired tilting angle.

An adjustable head holder for use with an imaging system having a table, the adjustable head holder having a tilt adjustment mechanism that will securely position a head at a plurality of different angles. The novelty being the tilt adjustment mechanism having a positive locking mechanism with a plurality of different notches that positively engage one end of the tilt adjustment bar to securely position the head holder without it slipping out of position if the patient lifts his/her head out of the head cradle.

Lockable adjustment (e.g., tilting) mechanism comprises a spring loaded tooth and ratchet adjustment mechanism.

The novelty is the positive locking mechanism, meaning if a patient lifts his/her head, the head holder won't move out of position to a different tilting angle, different from the desired tilting angle set by an imaging system operator or imaging technologist.

The adjustable head holder includes a head cradle, a table attachment that couples to an opening in the table, a tilt adjustment mechanism attached to the bottom of the head cradle at one end thereof, a tilt adjustment bar connecting the table attachment to the tilt adjustment mechanism, and a hinge connecting the head cradle to the table attachment.

The tilt adjustment mechanism and the tilt adjustment bar forming a positive locking mechanism.

The hinge is comprised of a flexible material connecting the carbon fiber head cradle to the table attachment. The flexible material may be carbon fiber, thermoplastic, plastic, rubber, or other flexible polymers, etc. The hinge allows for low material attenuation, torsional stiffness and provides the necessary range of motion of the adjustable head holder.

The tilt adjustment bar connects the table attachment to the tilt adjustment mechanism. The tilt adjustment bar may also be made of carbon fiber. The adjustable head holder is attached to the tilt adjustment mechanism with composite fasteners.

The tilt adjustment mechanism may include a biasing assembly, such as a spring-loaded tooth and ratchet assembly which allows for a patient's head to be tilted through a plurality of discrete angles (0, 10, 20, 30 degrees from horizontal, etc.). The tilt adjustment mechanism may be made of carbon fiber or injection molded plastic. The tilt adjustment mechanism includes a spring-loaded actuator. Compressing the spring-loaded actuator allows the tilt adjustment bar to extend into a ratchet opening at the desired tilt angle. The positive locking mechanism prevents the tilt angle to be adjusted once set by an imaging technologist or operator. The tilt adjustment mechanism includes a tilt angle of 0 degrees, so that an additional stationary head holder is not needed as the adjustable head holder functions both as a stationary head holder with a tilt angle of 0 degrees and an adjustable head holder with a plurality of tilt angles.

All of the components of the adjustable head holder are made of a non-metallic, low attenuation material to minimize the creation of image artifacts in the plane of view.

Turning now to FIGS. 3A and 3B, they show a first embodiment of an adjustable head holder 300. As described above, a user, such as subject 112 of FIG. 1, may have their head positioned on the adjustable head holder 300 to maintain a desired tilting angle of their head for imaging. CT imaging system 100 merely represents one exemplary usage of the adjustable head holder 300. As such, adjustable head holder 300 may be a non-limiting example of the head holder 116 of FIG. 1.

A coordinate system 390 is shown comprising three-axes, namely an x-axis parallel to a horizontal direction, a y-axis parallel to a vertical direction, and a z-axis perpendicular to each of the x- and y-axes. The adjustable head holder 300 comprises a central axis 399, which lies in a x-z plane.

The adjustable head holder 300 comprises a head cradle 302 which may receive a head of a patient. The head cradle 302 may comprise a body 304 with a first side 306 and a second side 308 extending therefrom. The body 304 comprises a substantially planar surface against which the patient's head may rest. The first side 306 and the second side 308 may extend from opposite edges of the body 304, wherein the sides are curved at the edges and flatten as they extend upward. The first side 306 and the second side 308 may function as boundaries that block the patient from moving their head off of the adjustable head holder 300.

A table attachment 310 may be coupled to a first end 392 of the head cradle 302 via a hinge 330. In one example, the table attachment 310 comprises carbon fiber and may be inserted into a table mount illustrated in FIG. 9. The head cradle 302 may also comprise carbon fiber. In one example, the hinge 330, which is physically coupled to the head cradle 302 and the table attachment 310, comprises a different material, such as rubber. More specifically, a first extension 322 of the table attachment 310 may extend angularly upward toward the head cradle 302, wherein the hinge 330 is physically coupled to each of the head cradle 302 and the table attachment 310. A close-up 380 illustrates a section view of the hinge 330 interfacing with the first extension 322 and the head cradle 302. The hinge 330 may be sandwiched between portions of the head cradle 302 and the first extension 322. More specifically, the hinge 330 may be partially surrounded by portions of the head cradle 302 and the first extension 322. A portion of the hinge 330 may be exposed through a gap 332 arranged between the head cradle 302 ad the first extension 322. The gap 332 may allow the hinge 330 to bend (e.g., flex) while remaining physically coupled to the head cradle 302 and the first extension 322. As illustrated, the hinge 330 is visible through the gap 332. A material of the hinge 330 may allow it to bend, wherein the material is rubber or another flexible material. In one example, the head cradle 302 and the table attachment 310 are inflexible (e.g., rigid) due to the carbon fiber, further comprising where bending of the hinge 330 results in an adjustment of an orientation of the head cradle 302 relative to the table attachment 310. In one example, only the head cradle 302 moves when the hinge 330 bends due to the table attachment 310 being physically coupled to a table on which the patient (e.g., subject 112 of FIG. 1) may be arranged. In one example, the table attachment 310 is physically coupled to a portion of the table on which a patient's neck may rest (e.g., a neck portion 382).

A first embodiment 340 and a second embodiment 350 of the hinge 330 are illustrated in the example of FIG. 3B. The first embodiment 340 comprises a substantially rectangular shape with a top surface 342 and a bottom surface 344. A width and length of the top surface 342 may be less than both a width and a length of the bottom surface 344. As such, a side surface 346 of the first embodiment 340 may be angled (e.g., tapered) as it extends from the bottom surface to the top surface. The first embodiment 340 further comprises an indentation 348 at which the first embodiment 340 may bend. The indentation 348 may correspond to a location of the hinge 330 exposed through the gap 332. The indentation 348 may be arranged at a middle (e.g., a center) of the first embodiment 340 between a first half 340A and a second half 340B, wherein the halves are identical in shape and size.

The second embodiment 350 also comprises a first half 350A and a second half 350B spaced about an indentation 358 and/or a joint/bend. The second embodiment 350 comprises a first plurality of openings 352 through which one or more fasteners may be inserted to physically couple the second embodiment to the head cradle 302. The second half 350B may comprise a second plurality of openings 354 through which fasteners may be inserted to physically couple the second embodiment to the table attachment 310.

The table attachment 310, which comprises the first extension 322, may further comprise a second extension 324, where both extensions extend away from the portion of the table attachment 310 received via the table mount. The second extension 324 may be coupled to a tilt adjustment bar 360. A coupling between the second extension 324 and the tilt adjustment bar 360 may be dynamic, wherein the coupling allows the tilt adjustment bar 360 to move relative to the second extension 324 without disengaging the coupling. In one example, the coupling is a revolute ball type joint, as will be desired in greater detail below.

The tilt adjustment bar 360, which may be interchangeably referred to as a tilt bar herein, is coupled to the revolute ball type joint at a first end and to a locking mechanism 370 at a second end, wherein the second end is opposite the first end. The bar 360 comprises a substantially rectangular shape, wherein the first end may comprise a contoured surface configured to engage with the revolute ball type joint. The second end may comprise a slot 362 which may engage with the locking mechanism 370, which enables the tilt adjustment bar 360 to actuate within the locking mechanism 370 without being removed from the locking mechanism 370 as will be described in greater detail below.

Thus, in the examples of FIGS. 3A and 3B, the locking mechanism 370 is arranged directly below the head holder 302. As such, the patient's head may be positioned directly above the locking mechanism 370 when imaging is occurring. The positioning of the locking mechanism 370 may allow an operator to easily adjust the head holder 302 from either side of the table. By positioning the revolute joint below the patient's neck area, complex parts entering an imaging range may be avoided, which may result in enhanced image quality and fewer image artifacts, if any.

Turning now to FIGS. 4A, 4B, 4C, 4D, and 4E, they show an embodiment 400 of the locking mechanism 370. As such, components previously introduced may be similarly numbered in this figure and in subsequent figures. The tilt adjustment bar 360 extends through an opening 402 into an interior space 404 of the locking mechanism 370. The tilt adjustment bar 360 comprises a first extreme end shaped as a rod 410 which is shaped via the slot 362. The rod 410 may comprise a rounded shape, wherein the rod 410 is configured to engage with one or more recesses 420 of the locking mechanism 370. Each recess of the one or more recesses 420 may correspond to a different position of the head holder (e.g., head holder 302 of FIG. 3A).

Each of the one or more recesses may be evenly spaced apart such that an adjustment of the head holder may be consistent as the rod 410 engages with different recesses. For example, actuating the rod 410 from a first recess to a second recess directly adjacent to the first recess may result in a positional adjustment of the head holder equal to a first magnitude. Actuating the rod 410 from the second recess to a third recess directly adjacent to the second recess may result in a positional adjustment of the head holder also equal to the second magnitude. As such, adjusting the rod 410 to engage with the third recess from the first recess results in a positional adjustment of twice the first magnitude. It will be appreciated that in some examples of the present disclosure a positional adjustment between adjacent recesses may not be uniform (e.g., equal).

In the example of FIGS. 4A and 4B, there are exactly three recesses. However, it will be appreciated that there may be greater than or less than three recesses without departing from the scope of the present disclosure. Furthermore, additionally or alternatively, a component may be arranged within each of the recesses such that a position of the recess may be fine-tuned to a more desirable position. In one example, the component may be a protrusion or the like which may adjust a position of the first rod 410 within the recess to adjust the tilt-angle via a lesser magnitude than moving the first rod to a different recess. For example, if a recess results in a 15-degree head holder position, then the component may be actuated to actuate a positioning of the rod 410 within the recess such that the angle of the head holder position is adjusted. In one example, the component may be configured to adjust the angle of the head holder position ±5 degrees.

Each recess of the plurality of recesses 420 may comprises a U-shaped cross-section, wherein the cross-section is taken along the x-y plane. A width of each recess of the plurality of recesses 420 may be correspondingly greater than a diameter of the rod 410 such that the rod 410 may be inserted into a recess without falling therefrom. That is to say, the rod 410, which comprises a cylindrical shape, may comprise a diameter correspondingly smaller than a width of each recess such that the rod 410 may minimally move in the x-direction when inserted into a recess.

The locking mechanism 370 may further comprise a switch 440. The switch 440 may be actuated along the y-direction. In one example, the switch 440 is actuated along the y-direction against a force of spring 460 via an operator to allow the rod 410 to free from a recess and move to a different recess. If the force applied by the operator does not exceed the force of the spring 460, then the switch 450 may not be actuated and the rod 410 may remain locked in place and engaged with the recess. As such, undesired (e.g., accidental) adjustment of the head holder via the operator or via the patient may be blocked. The spring may be a coil spring, leaf spring, or other resilient biasing element.

The plurality of recesses 420 and the first rod 410 are arranged between the at least one spring 460 and the switch 440. By configuring the locking mechanism 370 in this way, a packaging size and complexity of the locking mechanism 370 may be reduced.

Turning to FIG. 4F, it shows an embodiment of a revolute ball joint 480. As described above, the revolute ball joint 480 is arranged at an interface between a second end of the tilt adjustment bar 360 and the second extension 324. The second end is opposite the first end of the tilt adjustment bar 360, wherein the first end corresponds to the rod 410 of the tilt adjustment bar 360.

In one example, the rod 410 is a first rod 410, wherein the tilt adjustment bar 360 further comprises a second rod 482. The second rod 482 may be different than or equal to the first rod 410 in size. However, both rods may comprise a cylindrical shape. The second rod 482 may engage with a joint 484 of the second extension 324. The joint 484 may surround a majority (e.g., greater than 60% of a circumference) of the second rod 482, thereby blocking the second rod 482 from being removed from the joint 484 along the x- and y-axes. However, the second rod 482 may be removed from the joint 484 via being slid along the z-axis. It will be appreciated that motion of the second rod 482 along the z-axis does not correspond to an adjustment of the first rod 410 within the locking mechanism 370. Furthermore, the first rod 410 is contained within the interior space of the locking mechanism 370 such that its movement along the z-axis may be small to zero. In this way, removing the second rod 482 from the joint 484 may need some amount of disassembly of the present disclosure and may not occur during adjustment of the head holder.

The second rod 482 may be actuated within the joint 484. In one example, the second rod 482 may pivot within the joint 484 along direction 486 based on a movement of the first rod 410 within the interior space 404 of the locking mechanism 370. When the first rod 410 is inserted into a recess of the plurality of recesses 420, the second rod 482 may be blocked from pivoting within the joint 484. Movement of the first rod 410, the switch 450, and positions of the head holder are described in greater detail below.

Turning now to FIGS. 5A, 5B, and 5C, they show a first position 500, a second position 525, and a third position 550 of the head holder 302, respectively. FIGS. 5A, 5B, and 5C further illustrate a position of the first rod 410 within the locking mechanism 370.

In the first position 500, the head holder 302 may comprise an angle of zero degrees. As such, the head holder 302 may be in line with a table to which the table attachment 310 is physically coupled. By doing this, a patient's head may be relatively in line with their spine. In the first position, the first rod 410 is engaged with a first recess 420A of the plurality of recesses 420. The first recess 420A may be a recess furthest away from the table attachment 310.

In the second position 525, the head holder 302 may comprise an angle 330, which is greater than zero. In one example, the angle 330 is greater than five degrees and less than 50 degrees. In some examples, additionally or alternatively, the angle 330 is between 10 and 30 degrees. In some examples, the angle 330 is between 10 and 20 degrees. In one example, the angle 330 is equal to exactly 15 degrees.

The head holder 302 may be adjusted to the second position 525, from the first position 500, via pressing the switch 450 and actuating the first rod 410 from the first recess 420A to a second recess 420B. By doing this, a tilt of the patient's head may increase relative to the first position 500. This may be desired during imaging to avoid various artifacts that may arise due to dental work and the like.

In the third position 550, the head holder 302 may comprise an angle 352, which is greater than zero and greater than the angle 330. In one example, the angle 352 is between 15 and 50 degrees. In some examples, additionally or alternatively, the angle 352 is between 20 and 40 degrees. In some examples, additionally or alternatively, the angle 352 is between 25 and 35 degrees. In one example, the angle 352 is 30 degrees.

The head holder 302 may be adjusted to the third position 550, from the first position 500 or the second position 525, via pressing the switch 450 and inserting the first rod 410 into a third recess 420C. By doing this, the tilt of the patient's head may increase relative to each of the first and second positions 500, 525. One of the angles 330 and 352 may be selected based on an imaging of the patient's head that captures the fewest artifacts.

Turning now to FIGS. 6A, 6B, and 6C, they show a transition 600 from the first position 500 to the second position 525. More specifically, FIG. 6A illustrates the first position, FIG. 6B illustrates a transition position 625 between the first portion 500 and the second position 525, and FIG. 6C illustrates the second position 525.

To adjust the head holder from the first position 500 to the second position 525, the switch 450 is pressed in a first direction 602. In one example, the first direction 602 is an upward direction, opposite gravity. In one example, the switch 450 is moved via a push force, with a force greater than a threshold force of the at least one spring 460. If the push force is greater than or equal to the threshold force, then the at least one spring 460 compresses and the locking mechanism 370 moves to the transition position 625.

The transition position 625 illustrates pins 652 of the switch 450. The pins 652 are exposed due to a displacement of an upper portion of the switch 450 due to a compression of the at least one spring 460. When the at least one spring 460 is compressed, the switch 450 occupies a greater amount of the interior space of the locking mechanism 370. Furthermore, the plurality of recesses 420 are pressed upward into the at least one spring 460, thereby releasing the first rod 410.

The first rod 410 may be actuated within the interior space of the locking mechanism 370. In the example of FIG. 6C, the first rod 410 is actuated toward and inserted into the second recess 420B. As such, the second position 525 is selected in FIG. 6C. Once the first rod 410 is inserted into a desired recess of the plurality of recesses 420, the switch 450 may be released, wherein the switch 450 is pushed in a second direction 604, opposite the first direction 602. The at least one spring 460, which was previously compressed due to the force in the first direction 602, may now expand and push the switch 450 partially out of the interior space of the locking mechanism. By doing this, the at least one spring 460 may now occupy a greater amount of the interior space, and the first pin 410 may comprise less interior space for which to move out of the recess. In this way, the first pin 410 is locked in position. Pins 652 are still revealed in the embodiment of FIG. 6C to illustrate the downward engagement of the upper portion of the switch 450 with the pins 652.

Turning now to FIG. 6D, it illustrates an embodiment 650 of an outer surface 652 of the locking mechanism 370. The outer surface 652 is a visible surface of the locking mechanism 370 when the locking mechanism 370 is fully assembly. The outer surface 652 comprises a plurality of see-through holes 654 through which an operator may visualize with which of the recesses 420 the first rod 410 is engaged. In some examples, additionally or alternatively, the plurality of see-through holes 654 may comprise one or more markings, such as a protrusion, a recess, a bump, an ingot, and the like. As such, the operator may verify via feel or sight in which position the head holder is positioned.

Turning now to FIG. 7A, it shows a cross-section of a locking mechanism housing 700, which may be one example of a housing for the locking mechanism 370 of FIGS. 3A and 3B. The locking mechanism housing 700 comprises a shelf 702 arranged between an upper surface 704 and a bottom surface 706. The bottom surface 706 comprises a plurality of openings 708 through which a component (e.g., arms of the switch) may be arranged. As illustrated, the shelf 702 may be spaced away from each of the top surface 704 and the bottom surface 706 such that the shelf 702 is arranged within a middle portion of an interior space of the locking mechanism housing.

Proceeding to FIG. 7B, a positioning device 710 is inserted into the locking mechanism housing 700, wherein a rim 712 of the positioning device 710 is arranged directly above the shelf 702. As such, the rim 712 may rest upon the shelf 702 thereby setting a lowest position of the positioning device 710. As illustrated, the positioning device 710 may comprise the plurality of recesses 420, wherein a width of the rim 712 is greater than a width of the portion of the positioning device 710 comprising the plurality of recesses 420.

Proceeding to FIG. 7C, the first end of the tilt adjustment bar 360, which comprises the first rod 410, is inserted into a portion of the locking mechanism housing 700 below the positioning device 710. As such, the first rod 410 is arranged between the positioning device 710 and the bottom surface 706. Herein, the interior portion of the locking mechanism housing 700 between the shelf 702 and the bottom surface 706 is referred to as a lower interior portion 792. The interior portion of the locking mechanism housing 700 between the shelf 702 and the upper surface 704 is referred to as an upper interior portion 794.

Proceeding to FIG. 7D, the switch 450 is inserted into the lower interior portion 792 via the plurality of openings 708 arranged in the bottom surface 706 of the locking mechanism housing 700. The switch 450 comprises arms 750. A first arm 752 may extend through the slot 362 and a second arm 754 may not. As such, the first rod 410 may be positioned between the first arm 752 and the second arm 754. The first arm 752 and the second arm 754 may contact opposite ends of the positioning device 710.

Proceeding to FIG. 7E, the at least one spring 460 is inserted into the upper interior portion of the locking mechanism housing 700. As such, when the switch 450 is pressed toward the locking mechanism housing 700, the spring 460 may compress and a size of the upper interior portion 494 may decrease and a size of the lower interior portion 492 may increase. This may allow the first pin 410 to move out of a first recess and insert into a second recess. In one example, the at least one spring 460 is a leaf spring.

Proceeding to FIG. 7F, a fix stopper 760 may be arranged through the slot 362 and physically coupled to the upper surface 704. By doing this, the components in the interior space of the locking mechanism housing 700 may be blocked.

As illustrated, the structure illustrated provides for a plurality of discrete locking positions enabling variable adjustment of the tilt angle of a user's head when engaged with the head holding apparatus.

Turning now to FIG. 8, a second embodiment of an adjustable head holder 800 is shown. Components of the second embodiment of the adjustable head holder 800 identical to components of the first embodiments of the adjustable head holder 300 are similarly numbered in this figure and subsequent figures and are not reintroduced for reasons of brevity. It will be appreciated that the second embodiment of the adjustable head holder 800 is a non-limiting example of the adjustable head holder 116 of FIG. 1.

The second embodiment of the adjustable head holder 800 may be differentiated from the first embodiment of the adjustable head holder 300 in that it comprises a tilt adjustment bar 810, a table mount lock and release mechanism 820, a tilt bar 860, and a locking mechanism 870.

In one example, the second embodiment of the adjustable head holder 800 is configured for use with an imaging system having a table. The adjustable head holder 800 comprises a tilt adjustment mechanism 870 that will securely position a head at a plurality of different angles. One advantage being the tilt adjustment mechanism 700 comprises a positive locking mechanism with a plurality of different notches that positively engage one end of the tilt adjustment bar 860 to securely position the head holder 302 without it slipping out of position if the patient lifts his/her head out of the head cradle.

The adjustable head holder 800 includes a head cradle 302, a table attachment 310 that couples to an opening in the table (shown in FIG. 9), a tilt adjustment mechanism 870 attached to the bottom of the head cradle 302 at one end thereof opposite the table attachment 310, a tilt adjustment bar 860 connecting the table attachment 310 to the tilt adjustment mechanism 870, and a hinge 830 connecting the head cradle 302 to the table attachment 310.

The tilt adjustment mechanism 870 comprises a spring loaded tooth assembly 880 that may include a plurality of teeth 877 with a tooth opening 879 therebetween as shown further in FIG. 10 for example. The spring loaded tooth assembly 880 may also include a ratchet adjustment mechanism. A positive locking mechanism of the spring loaded tooth may function such that if a patient lifts his/her head, the head holder will not move out of position to a different tilting angle, different from the desired tilting angle set by an imaging system operator or imaging technologist. As such, the spring loaded tooth may urge the tilt adjustment bar 860 in an upward direction toward the head cradle 302. A further benefit of this positive locking mechanism may allow the operator to adjust the head cradle position via only one hand as a weight of the head cradle 302 is reduced via an opposite force of the spring loaded tooth.

The tilt adjustment mechanism 870 and the tilt adjustment bar form a positive locking mechanism. In example, the teeth 877 and spaces 879 are shaped to retain the tilt adjustment bar rod 864 with the forces holding the rod in place. In example, the angled surfaces of the spaces and teeth facilitate holding the bar in place when loaded with a user's head and when unloaded as well. For example, angled surface 892 is shown in phantom in FIG. 10 illustrates an example angle.

The hinge 830 is comprised of a flexible material connecting the carbon fiber head cradle 302 to the table attachment 310. The flexible material may be carbon fiber, thermoplastic, plastic, rubber, or other flexible polymers, etc. The hinge 830 allows for low material attenuation, torsional stiffness and provides the necessary range of motion of the adjustable head holder.

The tilt adjustment bar 860 connects the table attachment 310 to the tilt adjustment mechanism 870. The tilt adjustment bar may also be made of carbon fiber. The adjustable head holder 800 is attached to the tilt adjustment mechanism 870 with composite fasteners, in one example.

The tilt adjustment mechanism 870 includes a spring-loaded tooth and ratchet assembly 876 which allows for a patient's head to be tilted through a plurality of discrete angles (0, 10, 20, 30 degrees from horizontal parallel to the x-axis, etc.). The tilt adjustment mechanism 870 may be made of carbon fiber or injection molded plastic. The tilt adjustment mechanism includes a spring-loaded actuator. Compressing the spring-loaded actuator allows the tilt adjustment bar to extend into a ratchet opening at the desired tilt angle. The positive locking mechanism prevents the tilt angle to be adjusted once set by an imaging technologist or operator. The tilt adjustment mechanism includes a tilt angle of 0 degrees, so that an additional stationary head holder is not needed as the adjustable head holder functions both as a stationary head holder with a tilt angle of 0 degrees and an adjustable head holder with a plurality of tilt angles.

In an example, such as the example shown in FIG. 10, the spring loaded tooth assembly may have an integrated leaf spring 882, with a first end integrally coupled to a top of the bar 860 and extending downward and engages a top surface of the bottom wall 884 forming part of the opening 874. In an example, the integrated leaf spring is positioned in an inner area of the bar 860 and extends downward to slidingly engage, with a bias, the top surface of the bottom wall 884 at a contact point 886.

The tilt adjustment mechanism 870 comprises a first opening 872 facing the table mount 310. The first opening 872 allows the tilt adjustment bar 860 to enter an interior space of the tilt adjustment mechanism 870. The tilt adjustment mechanism further comprises a second opening 874, facing a direction parallel to the z-axis. In one example, the second opening 874 may function as a viewing window so that a user may visualize an exact position of the adjustable head holder 800.

The tilt adjustment bar 860 comprises a features which may engage with the ratchet system 876 so that a position of the adjustable head holder 800 may be locked. The tilt adjustment mechanism 870 is illustrated in greater detail with respect to FIG. 10.

Turning now to FIG. 9, a table 900 is shown. The table 900 comprises an opening 922 configured to receive a table mount 310 of the first or second embodiments of the adjustable head holder 300 or 800 of FIG. 3A or 8, respectively. The table comprises a top surface 912 opposite a bottom surface 914. The opening 922 is arranged directly between the top surface 912 and the bottom surface 914. The table 900 further comprises a first angled surface 916 and a second angled surface 918. In this way, the table 900 may comprise a trapezoidal shape, however, it will be appreciated that the table 900 may comprise other shapes, such as rectangular, square, or the like without departing from the scope of the present disclosure.

Turning now to FIG. 10, it shows a detailed view 1000 of the tilt adjustment mechanism 870 and an extreme end of the tilt adjustment bar 860 engaging with the tilt adjustment mechanism 870. In one example, the extreme end is a first extreme end, wherein a second extreme end of the tilt adjustment bar 860 is proximal to the table mount 310 of FIG. 8. The tilt adjustment bar 860 comprises a lever 862 and a rod 864. The tilt adjustment bar 860 may be similar to the tilt adjustment bar 360 of FIG. 3A in that it also comprises a first rod and a second rod, wherein the first rod engages with the tilt adjustment mechanism and the second rod engages with a ball joint. More specifically, the first rod may engage with a tooth of teeth of the ratchet system, wherein each tooth corresponds to a different tilt angle relative to the horizontal axis of the adjustable head holder. The lever 862 protrudes through a third opening 878 of the tilt adjustment mechanism 870 beyond a profile of the adjustable head holder 300. Said another way, a vertical axis 1099 extending from a horizontal most portion of the head cradle 302 intersects with the lever 862 such that the lever 862 extends farther in the horizontal direction than the head cradle 302. In this way, a user, such as an imaging technician, may assist a patient in placing their head on the adjustable head holder 300 while still being able to readily visualize and contact the lever 862.

As illustrated, the lever 862 comprises a ribbing, which includes a series of undulations such that the surface of the lever 862 is not smooth. In this way, the user may confirm contact with the lever 862 with their hand while the user is meeting the needs of the patient or performing another task. Additionally or alternatively, the lever 862 may comprise other markings in addition to or in place of the ribbing. The lever 862 may comprise dots, etchings, and other ingots to provide a sensatory feedback to the user.

Turning now to FIG. 11, it shows a detailed view 1100 of the first embodiment 340 of the hinge 330 incorporated into the second embodiment of the adjustable head holder 800. An extension arm 1130 extends from a table mount (e.g., table mount 310 of FIG. 8) toward the head cradle 302. The hinge 330 is in face sharing contact with bottom surfaces of the head cradle 302 and the extension arm 1130. In one example, the extension arm 1130 is shaped to conceal a majority of the hinge 330 in an overhead view of the adjustable head holder 800. As described above, the hinge 330 may be configured to pivot as the head cradle 302 is moved by a user and the adjustable tilt bar 860 is not in a locked position with the ratchet system 876.

Turning now to FIG. 12, it shows a side-on view 1200 of the adjustable head holder 800 mounted onto a table, such as table 900 of FIG. 9. More specifically, the table mount and release mechanism 820 comprises a protrusion 1210 pressed against the bottom surface 914 of the table. A force of the protrusion 1210 may block inadvertent dismounting of the adjustable head holder 800 from the table. That is to say, the adjustable head holder 800 may be fixedly mounted to the table until a tab 1212 is actuated, resulting in actuation of the protrusion 1210 in a direction away from the bottom surface 914, as illustrated via arrow 1214. When the protrusion 1210 is not pressed against the bottom surface 914, the adjustable head holder 800 may be dismounted (e.g., removed) from the table. As such, the table mount lock and release mechanism 820 may allow quick release of the adjustable head holder 800 from the table such that a different adjustable head holder may be mounted to for a subsequent patient.

In one aspect, a head holder may be adjusted via a locking mechanism comprising a switch. The combination of the locking mechanism and the switch may allow, quick, precise, and optimal positioning of a patient head. The technical effect of using the locking mechanism and the switch is to allow repeatable scans of a target area while allow an operator to easily adjust the head holder without allowing the patient to adjust the head holder. By doing this, medical imaging may be enhanced and patient outcomes improved.

An example of a system, comprises an adjustable head holder for use with an imaging system, the adjustable head holder comprising a head cradle, a tilt adjustment mechanism with a plurality of locking positions arranged below a first end of the head cradle, a table mount extending from a second end of the head cradle, and a tilt adjustment bar that extends from the table mount through the tilt adjustment mechanism, wherein the first end and the second end of the head cradle are located at opposite ends of the head cradle.

A first example of the system further includes where the tilt adjustment bar includes a lever that extends through an opening of the tilt adjustment mechanism.

A second example of the system, optionally including the first example, further includes where the tilt adjustment mechanism comprises a spring loaded tooth and a ratchet system.

A third example of the system, optionally including one or more of the previous examples, further includes where the adjustable head holder further comprises a hinge coupled between the second end of the head cradle and an extension arm extending from the table mount.

A fourth example of the system, optionally including one or more of the previous examples, further includes where the imaging system includes a table having an opening in one end thereof that is shaped to receive the table mount.

A fifth example of the system, optionally including one or more of the previous examples, further includes where the adjustable head holder further comprises a table mount lock and release mechanism coupled to the table mount.

A sixth example of the system, optionally including one or more of the previous examples, further includes where the imaging system is one of a computerized tomography (CT) imaging system, positron emission tomography (PET) imaging system, single-photon emission CT (SPECT) imaging system, or magnetic resonance imaging (MRI) system.

An example of an adjustable head holder for use with an imaging system, the adjustable head holder, comprising a head cradle, a tilt adjustment mechanism positioned below a first end of the head cradle, and a table mount extending from a second end of the head cradle, wherein the head cradle is configured to pivot via a hinge coupled to the second end of the head cradle and an extension arm of the table mount, and wherein the first end and the second end of the head cradle are located at opposite ends of the head cradle.

A first example of the adjustable head holder further includes where the hinge comprises a flexible material.

A second example of the adjustable head holder, optionally including the first example, further includes where the flexible material includes one or more of a carbon fiber, a thermoplastic, a plastic, a rubber, and a polymer.

A third example of the adjustable head holder, optionally including one or more of the previous examples, further includes where the table mount is inserted into an opening in one end of a table of the imaging system.

A fourth example of the adjustable head holder, optionally including one or more of the previous examples, further includes where the table mount comprises a table mount lock and release mechanism.

A fifth example of the adjustable head holder, optionally including one or more of the previous examples, further includes where the tilt adjustment mechanism receives a tilt adjustment bar extending from the table mount, wherein the tilt adjustment bar comprises a first rod configured to engage with a ratchet system of the tilt adjustment mechanism and a second rod arranged in a joint configured as a revolute ball joint.

A sixth example of the adjustable head holder, optionally including one or more of the previous examples, further includes where the first rod is arranged adjacent to a first end of the tilt adjustment bar and the second rod is arranged at a second end of the tilt adjustment bar opposite the first end, wherein the first end is a lever configured to actuate the first rod to and away from a ratchet system of the tilt adjustment mechanism.

A seventh example of the adjustable head holder, optionally including one or more of the previous examples, further includes where the lever extends through an opening of the tilt adjustment mechanism and beyond a profile of the head cradle in a horizontal direction.

An eighth example of the adjustable head holder, optionally including one or more of the previous examples, further includes where the adjustable head holder is adjustable relative to the horizontal direction.

An example of a system, comprises an adjustable head holder a table attachment coupled to a first half of a hinge via a first extension arm and the adjustable head holder coupled to a second half of the hinge, each of the table attachment and the adjustable head holder spaced apart from a bendable center of the hinge, and a tilt adjustment bar comprising a first rod adjacent to a lever on a first end of the tilt adjustment bar, the first rod configured to engage with a ratchet system of a tilt adjustment mechanism, the tilt adjustment bar further comprising a second rod at a second end of the tilt adjustment bar that is engaged with a joint of a second extension of the table attachment, wherein the second rod is configured to pivot within the joint, wherein the lever extends along a horizontal axis farther than a head cradle of the adjustable head holder and protrudes through an opening of the tilt adjustment mechanism.

A first example of the system further includes where the ratchet system includes a plurality of spring loaded teeth to engage the first rod of the tilt adjustment bar at a plurality of different tilt angles.

A second example of the system, optionally including the first example, further includes where the spring loaded teeth are configured to retain the first rod of the tilt adjustment bar in the ratchet system when the lever is not actuated.

A third example of the system, optionally including one or more of the previous examples, further includes where each tooth of the plurality of spring loaded teeth, corresponds to a different tilt angle of the adjustable head holder relative to the horizontal axis.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   an adjustable head holder for use with an imaging system, the adjustable head holder comprising:
   a head cradle;
   a tilt adjustment mechanism defining a plurality of discrete locking positions arranged below a first end of the head cradle, wherein the discrete locking positions include a plurality of recesses;
   a table mount extending from a second end of the head cradle;
   a tilt adjustment bar that extends from the table mount through the tilt adjustment mechanism, wherein the tilt adjustment bar includes a rod at one end configured to engage with the plurality of recesses, and wherein the tilt adjustment bar includes a lever that extends through an opening of the tilt adjustment mechanism; and
   wherein the first end and the second end of the head cradle are located at opposite ends of the head cradle.

2. The system of claim 1, wherein the tilt adjustment mechanism comprises a spring loaded tooth and a ratchet system.

3. The system of claim 1, wherein the adjustable head holder further comprises a hinge coupled between the second end of the head cradle and an extension arm extending from the table mount.

4. The system of claim 1, wherein the imaging system includes a table having an opening in one end thereof that is shaped to receive the table mount.

5. The system of claim 1, wherein the adjustable head holder further comprises a table mount lock and release mechanism coupled to the table mount.

6. The system of claim 1, wherein the imaging system is one of a computerized tomography (CT) imaging system, positron emission tomography (PET) imaging system, single-photon emission CT (SPECT) imaging system, or magnetic resonance imaging (MM) system.

7. An adjustable head holder for use with an imaging system, the adjustable head holder, comprising:
- a head cradle;
- a tilt adjustment mechanism including a plurality of recesses positioned below a first end of the head cradle, wherein the tilt adjustment bar includes a lever that extends through an opening of the tilt adjustment mechanism; and
- a table mount extending from a second end of the head cradle;
- wherein the head cradle is configured to pivot via a hinge coupled to the second end of the head cradle and an extension arm of the table mount; and
- wherein the first end and the second end of the head cradle are located at opposite ends of the head cradle;
- wherein the plurality of recesses of the tilt adjustment mechanism receives a tilt adjustment bar extending from the table mount, wherein the tilt adjustment bar comprises a first rod configured to engage with a ratchet system of the tilt adjustment mechanism and a second rod arranged in a joint configured as a revolute ball joint.

8. The adjustable head holder of claim 7, wherein the hinge comprises a flexible material.

9. The adjustable head holder of claim 8, wherein the flexible material includes one or more of a carbon fiber, a thermoplastic, a plastic, a rubber, and a polymer.

10. The adjustable head holder of claim 7, wherein the table mount is inserted into an opening in one end of a table of the imaging system.

11. The adjustable head holder of claim 7, wherein the table mount comprises a table mount lock and release mechanism.

12. The adjustable head holder of claim 1, wherein the rod is a first rod arranged adjacent to a first end of the tilt adjustment bar and a second rod is arranged at a second end of the tilt adjustment bar opposite the first end, wherein the first end is a lever configured to actuate the first rod to and away from a ratchet system of the tilt adjustment mechanism.

13. The adjustable head holder of claim 12, wherein the lever extends through an opening of the tilt adjustment mechanism and beyond a profile of the head cradle in a horizontal direction.

14. The adjustable head holder of claim 13, wherein the adjustable head holder is adjustable relative to the horizontal direction.

* * * * *